US012788691B2

(12) United States Patent
Raynaud et al.

(10) Patent No.: US 12,788,691 B2
(45) Date of Patent: Nov. 10, 2026

(54) TRANSPARENT AQUEOUS PERFUME COMPOSITION

(71) Applicant: V. MANE FILS, Le Bar-sur-Loup (FR)

(72) Inventors: Elsa Raynaud, Antibes (FR); Agnes Muratore, Chateauneuf-Grasse (FR)

(73) Assignee: V. Mane Fils, Le Bar-sur-Loup (FR)

( * ) Notice: Subject to any disclaimer, the term of this patent is extended or adjusted under 35 U.S.C. 154(b) by 454 days.

(21) Appl. No.: 18/292,982

(22) PCT Filed: Jul. 19, 2022

(86) PCT No.: PCT/EP2022/070254
§ 371 (c)(1),
(2) Date: Jan. 29, 2024

(87) PCT Pub. No.: WO2023/006523
PCT Pub. Date: Feb. 2, 2023

(65) Prior Publication Data

US 2024/0325259 A1 Oct. 3, 2024

(30) Foreign Application Priority Data

Jul. 30, 2021 (EP) .................................... 21306067

(51) Int. Cl.

| | |
|---|---|
| ***A61K 8/22*** | (2006.01) |
| ***A61K 8/06*** | (2006.01) |
| ***A61K 8/34*** | (2006.01) |
| ***A61K 8/41*** | (2006.01) |
| ***A61K 8/46*** | (2006.01) |
| ***A61K 8/92*** | (2006.01) |
| ***A61Q 13/00*** | (2006.01) |

(52) U.S. Cl.
CPC .............. *A61K 8/068* (2013.01); *A61K 8/345* (2013.01); *A61K 8/416* (2013.01); *A61K 8/466* (2013.01); *A61K 8/922* (2013.01); *A61Q 13/00* (2013.01); *A61K 2800/262* (2013.01); *A61K 2800/412* (2013.01)

(58) Field of Classification Search
None
See application file for complete search history.

(56) References Cited

U.S. PATENT DOCUMENTS

| | | | |
|---|---|---|---|
| 4,170,655 A | 10/1979 | Scheuermann et al. | |
| 4,299,737 A | 11/1981 | Meffert et al. | |
| 5,075,026 A | 12/1991 | Loth et al. | |
| 5,076,954 A | 12/1991 | Loth et al. | |
| 5,108,643 A | 4/1992 | Loth et al. | |
| 8,343,521 B2 | 1/2013 | Shick et al. | |
| 2002/0155078 A1* | 10/2002 | Avendano ................ | A61K 8/03 424/68 |
| 2008/0003247 A1 | 1/2008 | Shick et al. | |
| 2009/0208437 A1* | 8/2009 | Woehrmann ........... | A61K 31/14 514/23 |
| 2012/0097754 A1* | 4/2012 | Vlad ......................... | A61L 9/01 512/26 |
| 2013/0101531 A1 | 4/2013 | Shick et al. | |
| 2014/0357546 A1 | 12/2014 | Piechocki, II et al. | |
| 2016/0100574 A1 | 4/2016 | Pesaro et al. | |
| 2018/0208879 A1 | 7/2018 | Man et al. | |

FOREIGN PATENT DOCUMENTS

| | | |
|---|---|---|
| EP | 0278660 | 8/1988 |
| JP | 2001164466 A * | 6/2001 |

OTHER PUBLICATIONS

International Preliminary Report on Patentability for PCT/EP2022/070254 dated Jan. 18, 2024.
International Search Report for PCT/EP2022/070254 dated Nov. 14, 2022.
Written Opinion of the International Searching Authority for PCT/EP2022/070254 dated Nov. 14, 2022.

* cited by examiner

*Primary Examiner* — Tanisha Diggs
(74) *Attorney, Agent, or Firm* — B. Aaron Schulman, Esq.; Stites & Harbison PLLC

(57) ABSTRACT

A transparent, aqueous perfume micro-emulsion composition is provided that includes a fragrance material, a solvo-surfactant, an ionic surfactant, optionally a non-ionic surfactant, and water. The solvo-surfactant comprises at least one monoalkyl glycerol ether having a general formula of R—O—$CH_2$—CH(OH)—$CH_2$OH, wherein R is selected from the group consisting of C8 to C12 unbranched alkyls and C6 to C7 unbranched terminal alkenyls. The aqueous perfume microemulsions are stable and may be used in their concentrated form or diluted with water depending on the end use application.

13 Claims, No Drawings

TRANSPARENT AQUEOUS PERFUME COMPOSITION

FIELD OF THE INVENTION

The present invention relates generally to aqueous perfume compositions, and more particularly to transparent, aqueous perfume micro-emulsion compositions.

BACKGROUND

Traditionally, perfumes are provided dissolved in suitable solvents, which are typically lower aliphatic alcohols, such as ethanol, isopropanol, propylene glycol, glycol ethers, and other organic solvents and mixtures of such solvents with water. Perfumes intended for application to the skin are often dissolved in ethanol or in ethanol/water mixtures with a high ethanol content.

Ethanol and other lower aliphatic alcohols have several disadvantages as perfume solvents. They are volatile and flammable and thus present a fire hazard in production and use. They are relatively expensive and are not completely innocuous to health. Ethanol, which is the most acceptable of them from a health point of view, is heavily taxed in many countries and not allowed for religious reasons in some Islamic countries. Furthermore, ethanol and lower aliphatic alcohols have distinct odors, which may interfere with the perfume.

Thus, it would be advantageous to substantially eliminate these alcohols as perfume solvents and instead replace them with water, which is cheap, innocuous, non-flammable and odorless. However, most perfumes are substantially immiscible with water, and therefore such mixtures would necessarily be emulsions. To be suitable for applications where traditionally alcoholic solutions have been used, such emulsions should be thermodynamically stable and substantially clear, and thus should be a "micro-emulsion."

Perfume micro-emulsions in water comprising no, or only minor amounts of, ethanol are known in the art. However, the inherent hydrophobicity of most perfumes requires the presence of substantial quantities of surfactants as solubilizing agents. Surfactants which have been found suitable in the art for solubilizing perfumes in water have been anionics or mixtures thereof with smaller amounts of non-ionics. Thus, J. M. Blakeway et al, Int. J. Cosmet. Sc. 1, (1979), 1-15, described micro-emulsions containing up to 4% w/w perfume in water wherein at least 3 times the amount of sodium laurylether sulphate, monoethanolamine lauryl sulphate or combinations thereof, with a minor amount of coconut diethanolamide, were needed to obtain a clear micro-emulsion. T. J. Lin, Surfactants in Cosmetics, Surfactants Sci. Ser. Vol. 16, (1985), 29-52, mentions the necessity of having a surfactant to oil mass ratio of much greater than unity to prepare practical o/w micro-emulsions.

GB2190681A, EP0316726A and EP0368146A all describe clear aqueous perfume micro-emulsions for hard surface cleaning purposes. Although very wide theoretical limits for perfume, anionic surfactant, and non-ionic surfactant content are suggested, the disclosed examples only demonstrate surfactants in substantial excess to the amount of perfume. Most examples specify a surfactant/perfume ratio 7:1; one example specifies 7:3. The anionic/nonionic surfactant ratio is 4:3 in all examples. Furthermore, organic solvents, such as water-soluble lower alkanols of 2 to 4 carbon atoms, are preferably added as so-called co-surfactants.

Expired U.S. Pat. No. 4,170,655 discloses clear stable aqueous solutions of fat-soluble perfumes, wherein specific hydroxyalkylester- and/or N-(hydroxyalkyl)amide-ethoxylates are used in concentrations of 0.1-20% wt %, preferably 0.5-5 wt %, to solubilize 0.1-1% wt % of the perfume in the aqueous solution. Similarly, expired U.S. Pat. No. 4,299,737 discloses using hydroxyalkylether-propoxyethoxylates for the same purpose in the same relative amounts. In both of these expired U.S. patents, 7:3 and 8:2 surfactant/perfume ratios were used in all examples.

Expired EP0278660B describes clear homogeneous micro-emulsions containing at least 20% w/w of hydrophobic phase, at most 20% of hydrophilic phase, up to 20% of cationic quaternary ammonium surfactant, and a wide range of compounds suitable as co-surfactants. The hydrophilic phase may comprise appreciable quantities of alcohol.

WO2013095994A discloses the use of short-chain monoalkylglycerol ethers (substituted or unsubstituted C3 to C5 alkyl chain), which were reported as a new class of green solvo-surfactants by Queste et al. *Green Chem.*, 2006, 8, 822-830, as a replacement for 1,2-hexanediol or 1,2-heptanediol, which were used in various micro-emulsion formulations disclosed in WO2005123028A1.

While the foundational understanding of micro-emulsions seems to suggest micro-emulsions as formulations for aqueous based perfumes, it is also recognized that oil-in-water emulsions typically incorporate significant quantities of surfactants relative to the oil phase. The need for such large quantities of surfactants in oil-in-water emulsions will considerably limit the proportion of perfume that can be added to the mixture. In addition, many surfactants deliver olfactory responses that may mask, change or otherwise affect the olfactory response to the perfume component. This is why a disperse micro-emulsion may be unsuitable as a non-ethanol perfume delivery system. Furthermore, microbial growth tends to be problematic, even though typical preservatives can be added.

Therefore, there is a need to develop transparent aqueous perfume compositions that overcome one or more of the deficiencies of the traditional approaches, such as providing an efficient, optically clear, non-greasy, non-tacky fragrance micro-emulsion without altered or adulterated overtones of scent and that resist microbial growth.

SUMMARY

The present invention relates generally to aqueous perfume compositions. The invention is premised on the realization that transparent, aqueous perfume micro-emulsion compositions can be created by employing monoalkyl glycerol ether(s) having longer alkyl or alkylene chains, in the absence of ethanol or other short chain alcohols or diols.

According to embodiments of the present invention, a transparent, aqueous perfume micro-emulsion composition is provided, comprising (consisting essentially of, or consisting of):

(a) a fragrance material, wherein the fragrance material is present in an amount within a range of 3 wt % to 65 wt %;

(b) a solvo-surfactant, wherein the solvo-surfactant comprises, consists essentially of, or consists of, a monoalkyl glycerol ether having a general formula (I) of $R—O—CH_2—CH(OH)—CH_2OH$, wherein R is selected from the group consisting of C8 to C12 unbranched alkyls and C6 to C7 unbranched terminal alkenyls, wherein the solvo-surfactant is present in an amount within a range of 0.1 wt % to 25 wt %;

(c) an ionic surfactant present in an amount within a range of 0.5 wt % to 20 wt %;

(d) a non-ionic surfactant present in an amount within a range of 0 wt % to 20 wt %; and (e) quantum satis (q.s.) water;

wherein each wt % is based on the total weight of the micro-emulsion composition.

The present invention also relates to the use of a solvo-surfactant (b), as defined above, for preparing a transparent, aqueous perfume micro-emulsion composition.

The objects and advantages of the present invention will be further appreciated in light of the following detailed description and examples.

DETAILED DESCRIPTION

The present invention is premised on the realization that transparent, aqueous perfume micro-emulsion compositions are surprisingly created using monoalkyl glycerol ethers having longer (C8 to C12) unbranched alkyl or (C6 to C7) unbranched alkylene chains, in the absence of ethanol.

"Substantially free of ethanol", in the context of the invention, means that less than 1 weight percent (wt %), preferably less than 0.1 wt %, and more preferably no ethanol is intentionally added to the substance ("ethanol-free").

As used herein, "monoalkyl glycerol ether" or "MAGE" refers to glycerol-based compounds bearing only one unbranched alkyl or unbranched alkylene group on one of the primary hydroxyl groups of glycerol (1,2,3-trihydroxypropane), with the other two hydroxyl groups remaining unsubstituted. As used herein, MAGE compounds are "solvo-surfactants" useful toward forming transparent, aqueous perfume micro-emulsion compositions.

A "micro-emulsion" as the term is used herein denotes a pseudo one-phase transparent mixture of (i) two immiscible fluids, and (ii) at least one monoalkyl glycerol ether solvo-surfactant. Micro-emulsions are isotropic solutions, which can solubilize both water and oil, are thermodynamically stable and typically form spontaneously. They are stable by the presence of an interfacial film containing surface active molecules. Micro-emulsions are transparent, and do not display the opalescence of standard emulsions. There are several types of micro-emulsions, depending largely on the stiffness of the amphiphilic monolayer that separates the oily and the aqueous micro-domain. There are three types of micro-emulsions, oil-swollen micelles, water-swollen reverse micelles, and bicontinuous structures. The particle sizes of the resulting micelles or structures are small enough so the resulting mixture is optically clear.

For the purposes of the present invention, the term "optically clear" is used to define a composition that is "transparent" (i.e. transmitting light without distortion) which means that the size of the emulsion particles in the composition are reduced to a size where the particles are not observable with optical (visual) means. Turbidity/transparency of the micro-emulsion compositions were measured at room temperature on samples taken at various time intervals and aging temperatures: a) 1.5 h at room temperature, b) 24 h at 5° C. and 50° C., c) 1 week at 5° C. and 50° C., and d) 2 weeks at 5° C. and 50° C. Measurements of turbidity were performed at room temperature using a calibrated (per manufacturer's instructions and standards) turbidimeter: AQUALYTIC® TurbiDirect, taking an average of three (3) measurements done successively with the same sample and report in Nephelometric Turbidity Units (NTUs). As used herein, optically clear (transparent) aqueous perfume micro-emulsion compositions have a room temperature turbidity value of 12 NTU or less. Preferably, the inventive optically clear perfume micro-emulsions have a turbidity value, after aging at 2 weeks at 5° C. and 50° C., of 12 NTU or less.

In accordance with embodiments of the present invention, the aqueous perfume micro-emulsion composition, substantially free of ethanol, includes the following components: (a) a fragrance material; (b) a solvo-surfactant; (c) an ionic surfactant; (d) optionally a non-ionic surfactant; and (e) water. The aqueous perfume micro-emulsion composition may also optionally contain one or more additional ingredients, such as antioxidants, chelating agents, UV filters, preservatives, thickening agents, cosmetic active ingredients, moisturizers, humectants, emollients, opacifiers, pearly gloss impacting substances, pigments, colorants, dyes, and antifoaming agents.

The aqueous perfume micro-emulsion composition of the present invention includes one or more solvo-surfactant(s), wherein the solvo-surfactant(s) comprise(s), consist(s) essentially of, or consist(s) of, a monoalkyl glycerol ether having a general formula (I) of R—O—$CH_2$—CH(OH)—$CH_2$OH, wherein R is selected from the group consisting of C8 to C12 unbranched alkyls and C6 to C7 unbranched terminal alkenyls (i.e. C6 to C7 alkenyls in which the carbon-carbon double bond is at the end of the carbon chain). In one embodiment, R is selected from C8 to C12 unbranched alkyls, such as n-octyl, n-nonyl, n-decyl, or n-undecyl. In another embodiment, R is selected from C6 to C7 unbranched terminal alkenyls, such as hex-5-enyl or hept-6-enyl. Preferably, the monoalkyl glycerol ether solvo-surfactant(s) is/are selected from the group consisting of 1-octyl glycerol ether, 1-nonyl glycerol ether, 1-decyl glycerol ether, 1-undecyl glycerol ether, 1-hex-5-enyl glycerol ether, 1-hept-6-enyl glycerol ether, and combinations thereof. More preferably, the monoalkyl glycerol ether solvo-surfactant(s) is/are selected from the group consisting of 1-octyl glycerol ether, 1-decyl glycerol ether, and combinations thereof.

Other types of solvo-surfactants disclosed in the prior art, such as 1,2-hexanediol or 1-pentyl glycerol ether, are highly soluble in water. However, the solvo-surfactants within the scope of general formula (I) have relatively low solubility in water, yet are surprisingly efficient toward forming stable transparent aqueous perfume micro-emulsion compositions.

The amount of the solvo-surfactant present in the aqueous perfume micro-emulsion composition is generally from about a range of 0.1 wt % to 25 wt %; preferably from about 0.1 wt % to about 20 wt %, more preferably from about 0.5 wt % to about 20 wt %, and most preferably from about 0.5 wt % to about 15 wt %, with respect to the total weight of the aqueous perfume micro-emulsion composition.

The monoalkyl glycerol ethers may be synthesized using standard organic chemistry techniques, such as reacting glycidol with the appropriate alcohol under basic conditions. For example, 1-octyl glycerol ether may be synthesized by reacting 1-octanol and glycidol in the presence of a catalytic amount of sodium hydroxide. Alternatively, the monoalkyl glycerol ethers may be synthesized by alkylating solketal (2,2-dimethyl-4-((octyloxy)methyl)-1,3-dioxolane) with the appropriate alkyl or alkenyl halide, followed by hydrolysis of the acetonide protecting group. For example, 1-octyl glycerol ether may be synthesized by reacting 1-bromooctane and the anion of solketal, followed by acidic hydrolysis of the acetonide protecting group.

The aqueous perfume micro-emulsion composition of the present invention further includes an ionic surfactant, for example anionic, cationic, zwitterionic, and mixtures thereof, and may further include a non-ionic surfactant. Preferred surfactant combinations include mixtures of anionic surfactants and non-ionic surfactants, mixtures of cationic surfactants and non-ionic surfactants, and mixtures of zwitterionic surfactants and non-ionic surfactants.

Suitable anionic surfactants may include any conventional anionic surfactant. This may include a sulfate detersive surfactant, for e.g., alkoxylated and/or non-alkoxylated alkyl sulfate materials, and/or sulfonic detersive surfactants, e.g., alkyl benzene sulfonates. The anionic surfactants may be linear, branched, or combinations thereof. Non-limiting examples of anionic surfactants include C11 to C18 alkyl benzene sulfonates; primary or branched-chain C10 to C20 alkyl sulfates; unsaturated sulfates such as oleyl sulfate; C10 to C18 alkyl alkoxy sulfates, particularly those comprising 1-7 ethoxy groups; C10 to C18 alkyl alkoxy carboxylates, particularly those comprising 1-5 ethoxy groups; C10 to C18 alkyl polyglycosides and their corresponding sulfated polyglycosides, C12 to C18 alpha-sulfonated fatty acid esters, monoalkyl sulfosuccinates, and dialkyl sulfosuccinates. Other anionic surfactants useful herein are the water-soluble salts of alkyl phenol ethylene oxide ether sulfates and water-soluble salts of esters of alpha-sulfonated fatty acids. Anionic surfactants based on fatty acids include saturated and/or unsaturated fatty acids obtained from natural sources or synthetically prepared. Other exemplary anionic surfactants include acyl glycinate salts, such as sodium cocoyl glycinate; salts of acyl hydrolyzed wheat protein, such as sodium cocoyl hydrolyzed wheat protein, and cocoamphodiacetate salts, such as disodium cocoamphodiacetate. Other exemplary anionic surfactants include acyl glutamate salts, such as sodium cocoyl glutamate, sodium lauroyl glutamate, sodium caproyl glutamate, sodium myristoyl glutamate, sodium stearoyl glutamate, sodium oleoyl glutamate, sodium palmitoyl glutamate, or sodium linoleoyl glutamate; as well other anionic surfactants, such as sodium cocoyl sulfate, sodium isethionate, or sodium surfactin. Examples of suitable fatty acids include, but are not limited to, capric, lauric, myristic, palmitic, stearic, arachidic, and behenic acid. Other fatty acids include palmitoleic, oleic, linoleic, linolenic, and ricinoleic acid. Examples of monoalkyl sulfosuccinates include, but are not limited to, disodium monooctyl sulfosuccinate, and disodium laureth sulfosuccinate. Examples of suitable dialkyl sulfosuccinates include, but are not limited to, dioctyl sodium sulfosuccinate, ammonium dinonyl sulfosuccinate, diamyl sodium sulfosuccinate, dicapryl sodium sulfosuccinate, diethylhexyl sodium sulfosuccinate, diheptyl sodium sulfosuccinate, dihexyl sodium sulfosuccinate, diisobutyl sodium sulfosuccinate, ditridecyl sodium sulfosuccinate, and combinations thereof. Exemplary commercially available dioctyl sodium sulfosuccinate products include AEROSOL® OT-70 PG from Solvay (Brussels, Belgium), or TEGO® Sulfosuccinate DO 75 from Evonik Operations GmbH (Essen, Germany).

Suitable cationic surfactants include the quaternary ammonium surfactants such as alkyltrimethyl ammonium halogenides. Examples of suitable quaternary ammonium surfactants include, but are not limited to, cetrimonium chloride, coconut trimethyl ammonium chloride or bromide; coconut methyl dihydroxyethyl ammonium chloride or bromide; decyl triethyl ammonium chloride; decyl dimethyl hydroxyethyl ammonium chloride or bromide; C12 to C15 dimethyl hydroxyethyl ammonium chloride or bromide; coconut dimethyl hydroxyethyl ammonium chloride or bromide; myristyl trimethyl ammonium methyl sulphate; lauryl dimethyl benzyl ammonium chloride or bromide; lauryl dimethyl (ethenoxy)$_4$ ammonium chloride or bromide; and choline esters.

Suitable zwitterionic surfactants may include any conventional zwitterionic surfactant, such as betaines, including alkyl dimethyl betaine and cocodimethyl amidopropyl betaine, C8 to C18 (for example from C12 to C14) amine oxides (e.g., C12 to C14 dimethyl amine oxide), and/or sulfo and hydroxy betaines, such as N-alkyl-N,N-dimethylamino-1-propane sulfonate where the alkyl group can be C8 to C18, or from C10 to C14.

The ionic surfactant is present in the aqueous perfume micro-emulsion composition in an amount within a range of about 0.5 wt % to about 20 wt %, such as from about 3 wt % to about 19 wt %, and more preferably from about 5 wt % to about 18 wt %, with respect to the total weight of the aqueous perfume micro-emulsion composition.

In accordance with an embodiment of the present invention, the aqueous perfume micro-emulsion composition of the present invention may further comprise a nonionic surfactant. Suitable nonionic surfactants include alkoxylated fatty alcohols, such as ethoxylated fatty alcohols. Other suitable nonionic surfactants include alkoxylated alkyl phenols, alkyl phenol condensates, mid-chain branched alcohols, mid-chain branched alkyl alkoxylates, alkylglucosides, alkylpolysaccharides (e.g., alkylpolyglycosides), polyhydroxy fatty acid amides, ether capped poly(oxyalkylated) alcohols, polyglyceryl esters, and mixtures thereof. The alkoxylate units may be ethyleneoxy units, propyleneoxy units, or mixtures thereof. The nonionic surfactants may be linear, branched (e.g., mid-chain branched), or a combination thereof. Specific nonionic surfactants may include alcohols having an average of from about 12 to about 16 carbons, and an average of from about 3 to about 9 ethoxy groups, such as C12 to C14 EO7 nonionic surfactant. Exemplary non-ionic surfactants include ethoxylated alkylphenol ethers, particularly octyl- and nonylphenol ethers containing 5-20 EO; ethoxylated aliphatic C6 to C20 alcohols, which may be linear or branched and include Guerbet-type alcohols, containing 2-30 EO; ethoxylated sterols containing 5-20 EO; polyethylene glycol (2-10 EO) mono- and diesters of aliphatic C5 to C11 carboxylic acids; ethoxylated castor oil or hydrogenated caster oil derivatives containing 10-60 EO, such as PEG-40 hydrogenated castor oil (e.g., CREMOPHOR® RH 40; BASF, Germany). No-limiting examples of suitable nonionic surfactants include polyglyceryl-4-caprate, decyl glucoside or polyglucoside, lauryl glucoside or polyglucoside, coco-glucoside or polyglucoside, or PEG-40 hydrogenated castor oil.

The amount of the (optional) non-ionic surfactant present in the aqueous perfume micro-emulsion composition is generally present in an amount within a range of 0 wt % to about 20 wt %. When the non-ionic surfactant is present in the composition, the amount of surfactant is preferably from about 0.5 wt % to about 20 wt %, and more preferably from about 2 wt % to about 15 wt %, with respect to the total weight of the aqueous perfume micro-emulsion composition.

Examples of preferred surfactant systems include combinations of anionic and non-ionic surfactants. Examples of particularly preferred surfactants include combinations of anionic and non-ionic surfactants, such as a combination of a dialkyl sulfosuccinate and an ethoxylated hydrogenated castor oil. In one embodiment, the surfactants used in combination with the monoalkyl glycerol ether solvo-surfactant(s) include a mixture of dioctyl sodium sulfosuccinate and PEG-40 hydrogenated castor oil.

The total amount of surfactants (ionic and nonionic) which may be used in the composition of the present invention is generally in a range from about 0.5 wt % to about 45 wt %, preferably from about 5 wt % to about 40 wt %, more preferably from 10 to about 30 wt % and most preferably from about 15 to about 25 wt %, with respect to the total weight of the aqueous perfume micro-emulsion composition.

In accordance with an embodiment of the present invention, a mass ratio between a mass of the fragrance material and a combined masses of the solvo-surfactant/surfactant(s) is generally from 1:1 to 10:1, preferably from 1:1 to 6:1, more preferably from 1:1 to 5:1, and most preferably from 1:1 to 4:1.

In a further aspect, the solvo-surfactant(s) within the scope of general formula (I) may be used in combination with other known solvo-surfactant(s), which are outside the scope of general formula (I). For example, the present solvo-surfactant(s) within the scope of general formula (I) may be used in combination with a 1,2-alkane diol, such as 1,2-pentanediol, 1,2-hexanediol, 1,2-octanediol, or mixtures thereof; butylene glycol; a short-chain (C1 to C5) monoalkyl glycerol ether, such as 1-butyl glycerol ether; an isosorbide derivative, such as endo and exo forms of propylisosorbide, butylisosorbide, pentylisosorbide, or dimethyl isosorbide; di-isopropylidene glycerol (solketal or Augeo® crystal), or mixtures thereof; or a mixture of two or more of the foregoing. If such combination is utilized, the mass ratio between the solvo-surfactant of general formula (I) and the alternative known solvo-surfactant(s) may be from 100:1 to 1:1, preferably from 10:1 to 1:1. In another embodiment, the aqueous perfume micro-emulsion may be void of any 1,2-alkanediols, short chain (C1 to C5) monoalkylglycerol ethers, and/or isosorbide derivatives.

The aqueous perfume micro-emulsion composition of the present invention includes one or more fragrance materials (a), such as natural and/or synthetic fragrance raw materials. Of particular interest are oil soluble perfume oils, which may or may not be in a mixture with water-soluble perfume oils, and individual fragrance compounds. The oil soluble perfume oils may be natural, or nature-identical essential oils selected from the group consisting of extracts of natural raw materials such as essential oils, concretes, absolutes, resins, resinoids, balsams, tinctures such as for example ambergris tincture; amyris oil; *angelica* seed oil; *angelica* root oil; aniseed oil; valerian oil; basil oil; tree moss absolute; bay oil; armoise oil; benzoin resin; bergamot oil; beeswax absolute; birch tar oil; bitter almond oil; savory oil; buchu leaf oil; cabreuva oil; cade oil; calamus oil; camphor oil; *cananga* oil; cardamom oil; cascarilla oil; *cassia* oil; cassie absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill weed oil; dill seed oil; eau de brouts absolute; oak moss absolute; elemi oil; tarragon oil; *Eucalyptus citriodora* oil; *eucalyptus* oil; fennel oil; fir needle oil; *galbanum* oil; *galbanum* resin; geranium oil; grapefruit oil; guaiac wood oil; gurjun balsam; gurjun balsam oil; helichrysum absolute; helichrysum oil; ginger oil; iris root absolute; iris root oil; jasmine absolute; calamus oil; blue chamomile oil; Roman chamomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemon-grass oil; lovage oil; lime oil distilled; lime oil expressed; linaloe oil; *Litsea cubeba* oil; laurel leaf oil; mace oil; marjoram oil; mandarin oil; massoi bark oil; *mimosa* absolute; ambrette seed oil; musk tincture; clary sage oil; nutmeg oil; myrrh absolute; myrrh oil; myrtle oil; clove leaf oil; clove bud oil; neroli oil; olibanum absolute; olibanum oil; opopanax oil; orange flower absolute; orange oil; *origanum* oil; palmarosa oil; patchouli oil; *perilla* oil; Pew balsam oil; parsley leaf oil; parsley seed oil; petitgrain oil; peppermint oil; pepper oil; pimento oil; pine oil; pennyroyal oil; rose absolute; rosewood oil; rose oil; rosemary oil; Dalmatian sage oil; Spanish sage oil; sandalwood oil; celery seed oil: spike-lavender oil; star anise oil; *styrax* oil; *tagetes* oil; fir needle oil; tea tree oil; turpentine oil; thyme oil; Tolu balsam; tonka bean absolute; tuberose absolute; vanilla extract; violet leaf absolute; *verbena* oil; vetiver oil; juniper berry oil; wine lees oil; wormwood oil; wintergreen oil; ylang-ylang oil; hyssop oil; civet absolute; cinnamon leaf oil; cinnamon bark oil, and also fractions thereof, or ingredients isolated therefrom.

Additionally, one or more fragrance materials may be selected from individual odorous substances from the group of the hydrocarbons; aliphatic aldehydes and acetals thereof, aliphatic ketones and oximes thereof; aliphatic sulfur-containing compounds; aliphatic nitriles; esters of aliphatic carboxylic acids; formates, acetates, propionates, isobutyrates, butyrates, isovalerates, pentanoates, hexanoates, crotonates, tiglinates or 3-methyl-2-butenoates of acyclic or cyclic terpene alcohols; acyclic terpene aldehydes and ketones; cyclic terpene aldehydes and ketones; cyclic and cycloaliphatic ethers; cyclic and macrocyclic ketones; cycloaliphatic aldehydes and ketones, esters of cyclic and cycloaliphatic alcohols; esters of cycloaliphatic carboxylic acids, esters of araliphatic alcohols and aliphatic carboxylic acids; araliphatic ethers; aromatic and araliphatic aldehydes; aromatic and araliphatic ketones; aromatic and araliphatic carboxylic acids and esters; nitrogen-containing aromatic compounds; phenyl ethers and phenyl esters; heterocyclic compounds; and combinations thereof.

Exemplary hydrocarbons include, but are not limited to, 3-carene, alpha-pinene, beta-pinene, alpha-terpinene, gamma-terpinene, p-cymene, bisabolene, camphene, caryophyllene, cedrene, farnesene, limonene, longifolene, myrcene, ocimene, valencene, (E,Z)-1,3,5-undecatriene, styrene, and diphenylmethane.

Exemplary aliphatic aldehydes and acetals thereof include, but are not limited to, hexanal, heptanal, octanal, nonanal, decanal, undecanal, dodecanal, tridecanal, 2-methyloctanal, 2-methylnonanal, (E)-2-hexenal, (Z)-4-heptenal, 2,6-dimethyl-5-heptenal, 10-undecenal, (E)-4-decenal, 2-dodecenal, 2,6,10-trimethyl-9-undecenal, 2,6,10-trimethyl-5,9-undecadienal, heptanal diethyl acetal, 1,1-dimethoxy-2,2,5-trimethyl-4-hexene, citronellyloxyacetaldehyde, and 1-(1-methoxypropoxy)-(E/Z)-3-hexene.

Exemplary aliphatic ketones and oximes thereof include, but are not limited to, 2-heptanone, 2-octanone, 3-octanone, 2-nonanone, 5-methyl-3-heptanone, 5-methyl-3-heptanone oxime, 2,4,4,7-tetramethyl-6-octen-3-one, and 6-methyl-5-hepten-2-one.

Exemplary aliphatic sulfur-containing compounds include, but are not limited to, 3-methylthiohexanol, 3-methylthiohexyl acetate, 3-mercaptohexanol, 3-mercaptohexyl acetate, 3-mercaptohexyl butyrate, 3-acetylthiohexyl acetate, and 1-menthene-8-thiol.

Exemplary aliphatic nitriles include, but are not limited to, 2-nonenoic acid nitrile, 2-undecenoic acid nitrile, 2-tridecenoic acid nitrile, 3,12-tridecadienoic acid nitrile, 3,7-dimethyl-2,6-octadienoic acid nitrile, and 3,7-dimethyl-6-octenoic acid nitrile.

Exemplary esters of aliphatic carboxylic acids include, but are not limited to, (E)- and (Z)-3-hexenyl formate, ethyl acetoacetate, isoamyl acetate, hexyl acetate, 3,5,5-trimethyl hexyl acetate, 3-methyl-2-butenyl acetate, (E)-2-hexenyl acetate, (E)- and (Z)-3-hexenyl acetate, octyl acetate, 3-octyl acetate, 1-octen-3-yl acetate, ethyl butyrate, butyl butyrate, isoamyl butyrate, hexyl butyrate, (E)- and (Z)-3-hexenyl isobutyrate, hexyl crotonate, ethyl isovalerate, ethyl-2-methyl pentanoate, ethyl hexanoate, allyl hexanoate, ethyl heptanoate, allyl heptanoate, ethyl octanoate, ethyl-(E,Z)-2,4-decadienoate, in particular ethyl-2-trans-4-cis-decadienoate, methyl-2-octinate, methyl-2-noninate, allyl-2-isoamyloxyacetate, methyl-3,7-dimethyl-2,6-octadienoate, and 4-methyl-2-pentyl crotonate.

Exemplary formates, acetates, propionates, isobutyrates, butyrates, isovalerates, pentanoates, hexanoates, crotonates, tiglinates or 3-methyl-2-butenoates of acyclic and cyclic terpene alcohols include, but are not limited to, those esters derived from acyclic alcohols such as citronellol, geraniol, nerol, linalool, lavandulol, nerolidol, farnesol, tetrahydrolinalool, tetrahydrogeraniol, 2,6-dimethyl-7-octen-2-ol, 2,6-dimethyloctan-2-ol, 2-methyl-6-methylene-7-octen-2-ol, 2,6-dimethyl-5,7-octadien-2-ol, 2,6-dimethyl-3,5-octadien-2-ol, 3,7-dimethyl-4,6-octadien-3-ol, 3,7-dimethyl-1,5,7-octatrien-3-ol, and 2,6-dimethyl-2,5,7-octatrien-1-ol; and those esters derived from cyclic terpene alcohols such as menthol, isopulegol, alpha-terpineol, terpinenol-4, menthan-8-01, menthan-1-ol, menthan-7-ol, borneol, isoborneol, linalool oxide, nopol, cedrol, ambrinol, vetiverol, and guaiol.

Exemplary acyclic terpene aldehydes and ketones, include but are not limited to, geranial, neral, citronellal, 7-hydroxy-3,7-dimethyloctanal, 7-methoxy-3,7-dimethyloctanal, 2,6,10-trimethyl-9-undecenal, geranyl acetone, and also dimethyl and diethyl acetals thereof, such as the dimethyl and diethyl acetals of geranial, neral, and 7-hydroxy-3,7-dimethyloctanal.

Exemplary cyclic terpene aldehydes and ketones include, but are not limited to, menthone, isomenthone, 8-mercaptomenthan-3-one, carvone, camphor, fenchone, alpha-ionone, beta-ionone, alpha-n-methyl ionone, beta-n-methyl ionone, alpha-isomethyl ionone, beta-isomethyl ionone, alpha-irone, alpha-damascone, beta-damascone, beta-damascenone, delta-damascone, gamma-damascone, 1-(2,4,4-trimethyl-2-cyclohexen-1-yl)-2-buten-1-one, 1,3,4,6,7,8a-hexahydro-1,1,5,5-tetramethyl-2H-2,4a-methanonaphthalen-8(5H)-one, 2-methyl-4-(2,6,6-trimethyl-1-cyclohexen-1-yl)-2-butenal, nootkatone, dihydronootkatone, 4,6,8-megastigmatrien-3-one, alpha-sinensal, beta-sinensal, and acetylated cedar wood oil (methylcedryl ketone).

Exemplary cyclic and cycloaliphatic ethers include, but are not limited to, cineole, cedryl methyl ether, cyclododecyl methyl ether, 1,1-dimethoxycyclododecane, (ethoxymethoxy)cyclododecane, alpha-cedrene epoxide, 3a,6,6,9a-tetramethyldodecahydronaphtho[2,1-b]furan, 3a-ethyl-6,6,9a-trimethyldodecahydronaphtho[2,1-b]furan, 1,5,9-trimethyl-13-oxabicyclo[10.1.0]trideca-4,8-diene, rose oxide, and 2-(2,4-dimethyl-3-cyclohexen-1-yl)-5-methyl-5-(1-methylpropyl)-1,3-dioxane.

Exemplary cyclic and macrocyclic ketones include, but are not limited to, 4-tert-butylcyclohexanone, 2,2,5-trimethyl-5-pentylcyclopentanone, 2-heptylcyclopentanone, 2-pentylcyclopentanone, 2-hydroxy-3-methyl-2-cyclopenten-1-one, 3-methyl-cis-2-penten-1-yl-2-cyclopenten-1-one, 3-methyl-2-pentyl-2-cyclopenten-1-one, 3-methyl-4-cyclopentadecenone, 3-methyl-5-cyclopentadecenone, 3-methylcyclopentadecanone, 4-(1-ethoxyvinyl)-3,3,5,5-tetramethylcyclohexanone, 4-tert-pentylcyclohexanone, 5-cyclohexadecen-1-one, 6,7-dihydro-1,1,2,3,3-pentamethyl-4(5H)-indanone, 8-cyclohexadecen-1-one, 7-cyclohexadecen-1-one, (7/8)-cyclohexadecen-1-one, 9-cycloheptadecen-1-one, cyclopentadecanone, and cyclohexadecanone.

Exemplary cycloaliphatic aldehydes and ketones include, but are not limited to, 2,4-dimethyl-3-cyclohexene carbaldehyde, 2-methyl-4-(2,2,6-trimethylcyclohexen-1-yl)-2-butenal, 4-(4-hydroxy-4-methylpentyl)-3-cyclohexenecarbaldehyde, 4-(4-methyl-3-penten-1-yl)-3-cyclohexene carbaldehyde, 1-(3,3-dimethylcyclohexyl)-4-penten-1-one, 2,2-dimethyl-1-(2,4-dimethyl-3-cyclohexen-1-yl)-1-propanone, 1-(5,5-dimethyl-1-cyclohexen-1-yl)-4-penten-1-one, 2,3,8,8-tetramethyl-1,2,3,4,5,6,7,8-octahydro-2-naphthalenyl methyl ketone, methyl-2,6,10-trimethyl-2,5,9-cyclododecatrienyl ketone, and tert-butyl-(2,4-dimethyl-3-cyclohexen-1-yl) ketone.

Exemplary esters of cyclic and cycloaliphatic alcohols include, but are not limited to, 2-tert-butylcyclohexyl acetate, 4-tert-butylcyclohexyl acetate, 2-tert-pentylcyclohexyl acetate, 4-tert-pentylcyclohexyl acetate, 3,3,5-trimethylcyclohexyl acetate, decahydro-2-naphthyl acetate, 2-cyclopentylcyclopentyl crotonate, 3-pentyltetrahydro-2H-pyran-4-yl acetate, decahydro-2,5,5,8a-tetramethyl-2-naphthyl acetate, 4,7-methano-3a,4,5,6,7,7a-hexahydro-5- or 6-indenyl acetate, 4,7-methano-3a,4,5,6,7,7a-hexahydro-5- or 6-indenyl propionate, 4,7-methano-3a,4,5,6,7,7a-hexahydro-5- or 6-indenyl isobutyrate, 4,7-methanooctahydro-5- or 6-indenyl acetate, and 1-cyclohexylethyl crotonate.

Exemplary esters of cycloaliphatic carboxylic acids include, but are not limited to, allyl-3-cyclohexyl propionate, allylcyclohexyl oxyacetate, cis- and trans-methyl dihydrojasmonate, cis- and trans-methyl jasmonate, methyl-2-hexyl-3-oxocyclopentane carboxylate, ethyl-2-ethyl-6,6-dimethyl-2-cyclohexene carboxylate, ethyl-2,3,6,6-tetramethyl-2-cyclohexene carboxylate, and ethyl-2-methyl-1,3-dioxolane-2-acetate.

Exemplary esters of araliphatic alcohols and aliphatic carboxylic acids include, but are not limited to, benzyl acetate, benzyl propionate, benzyl isobutyrate, benzyl isovalerate, 2-phenylethyl acetate, 2-phenylethyl propionate, 2-phenylethyl isobutyrate, 2-phenylethyl isovalerate, 1-phenylethyl acetate, alpha-trichloromethylbenzyl acetate, alpha,alpha-dimethylphenylethyl acetate, alpha,alpha-dimethylphenylethyl butyrate, cinnamyl acetate, 2-phenoxyethyl isobutyrate, and 4-methoxybenzyl acetate.

Exemplary araliphatic ethers include, but are not limited to, 2-phenylethyl methyl ether, 2-phenylethyl isoamyl ether, 2-phenylethyl 1-ethoxyethyl ether, phenyl acetaldehyde dimethyl acetal, phenyl acetaldehyde diethyl acetal, hydratropaldehyde dimethyl acetal, phenyl acetaldehyde glycerol acetal, 2,4,6-trimethyl-4-phenyl-1,3-dioxane, 4,4a,5,9b-tetrahydroindeno[1,2-d]-m-dioxin, and 4,4a,5,9b-tetrahydro-2,4-dimethylindeno[1,2-d]-m-dioxin.

Exemplary aromatic and araliphatic aldehydes include, but are not limited to, benzaldehyde, phenylacetaldehyde, 3-phenylpropanal, hydratropaldehyde, 4-methylbenzaldehyde, 4-methylphenylacetaldehyde, 3-(4-ethylphenyl)-2,2-dimethylpropanal, 2-methyl-3-(4-isopropylphenyl)propanal, 2-methyl-3-(4-tert-butyl phenyl)propanal, 2-methyl-3-(4-isobutylphenyl)propanal, 3-(4-tert-butylphenyl)propanal, cinnamaldehyde, alpha-butylcinnamaldehyde, alpha-amylcinnamaldehyde, alpha-hexylcinnamaldehyde, 3-methyl-5-phenylpentanal, 4-methoxybenzaldehyde, 4-hydroxy-3-methoxybenzaldehyde, 4-hydroxy-3-ethoxybenzaldehyde, 3,4-methylenedioxybenzaldehyde, 3,4-dimethoxybenzaldehyde, 2-methyl-3-(4-methoxyphenyl)propanal, and 2-methyl-3-(4-methylenedioxyphenyl)propanal.

Exemplary aromatic and araliphatic ketones include, but are not limited to, acetophenone, 4-methylacetophenone, 4-methoxyacetophenone, 4-tert-butyl-2,6-dimethylacetophenone, 4-phenyl-2-butanone, 4-(4-hydroxyphenyl)-2-butanone, 1-(2-naphthalenyl)ethanone, 2-benzofuranylethanone, (3-methyl-2-benzofuranyl)ethanone, benzophenone, 1,1,2,3,3,6-hexamethyl-5-indanyl methyl ketone, 6-tert-butyl-1,1-dimethyl-4-indanyl methyl ketone, 1-[2,3-dihydro-1,1,2,6-tetramethyl-3-(1-methylethyl)-1H-5-indenyl] ethanone, and 5',6',7',8'-tetrahydro-3,5,5,6,8,8-hexamethyl-2-acetonaphthone.

Exemplary aromatic and araliphatic carboxylic acids and esters thereof include, but are not limited to, benzoic acid, phenylacetic acid, methyl benzoate, ethyl benzoate, hexyl benzoate, benzyl benzoate, methylphenyl acetate, ethylphenyl acetate, geranylphenyl acetate, phenylethylphenyl acetate, methyl cinnamate, ethyl cinnamate, benzyl cinnamate, phenylethyl cinnamate, cinnamyl cinnamate, allyl phenoxy acetate, methyl salicylate, isoamyl salicylate, hexyl salicylate, cyclohexyl salicylate, cis-3-hexenyl salicylate, benzyl salicylate, phenylethyl salicylate, methyl-2,4-dihydroxy-3,6-dimethylbenzoate, ethyl-3-phenyl glycidate, and ethyl-3-methyl-3-phenyl glycidate.

Exemplary nitrogen-containing aromatic compounds include, but are not limited to, 2,4,6-trinitro-1,3-dimethyl-5-tert-butylbenzene, 3,5-dinitro-2,6-dimethyl-4-tert-butyl acetophenone, cinnamonitrile, 3-methyl-5-phenyl-2-pentenoic acid nitrile, 3-methyl-5-phenylpentanoic acid nitrile, methyl anthranilate, methyl-N-methyl anthranilate, Schiff bases of methyl anthranilate with 7-hydroxy-3,7-dimethyloctanal, 2-methyl-3-(4-tert-butylphenyl)propanal or 2,4-dimethyl-3-cyclohexenecarbaldehyde, 6-isobutyl quinolone, 6-sec-butyl quinolone, 2-(3-phenylpropyl)pyridine, indole, skatole, 2-methoxy-3-isopropylpyrazine, and 2-isobutyl-3-methoxypyrazine.

Exemplary phenyl ethers and phenyl esters include, but are not limited to, estragole, anethole, eugenyl methyl ether, isoeugenyl methyl ether, diphenyl ether, beta-naphthyl methyl ether, beta-naphthyl ethyl ether, beta-naphthyl isobutyl ether, 1,4-dimethoxybenzene, eugenyl acetate, and p-cresyl phenyl acetate.

Exemplary heterocyclic compounds include, but are not limited to, 2,5-dimethyl-4-hydroxy-2H-furan-3-one, 2-ethyl-4-hydroxy-5-methyl-2H-furan-3-one, 3-hydroxy-2-methyl-4H-pyran-4-one, 2-ethyl-3-hydroxy-4H-pyran-4-one, and lactones such as 1,4-octanolide, 3-methyl-1,4-octanolide, 1,4-nonanolide, 1,4-decanolide, 8-decen-1,4-olide, 1,4-undecanolide, 1,4-dodecanolide, 1,8-decanolide, 1,5-dodecanolide, 4-methyl-1,4-decanolide, 1,15-pentadecanolide, cis- and trans-11-pentadecen-1,15-olide, cis- and trans-12-pentadecen-1,15-olide, 1,16-hexadecanolide, 9-hexadecen-1,16-olide, 10-oxa-1,16-hexadecanolide, 11-oxa-1, 16-hexadecanolide, 12-oxa-1,16-hexadecanolide, ethylene-1,12-dodecanedioate, ethylene-1,13-tridecanedioate, coumarin, 2,3-dihydrocoumarin, and octahydrocoumarin. Further examples of odorous substances are known from literature, such as from the book “Perfume and Flavor Chemicals”, edited by S. Arctander, 1969, Montclair N.J. (USA).

The aqueous perfume micro-emulsion composition advantageously includes about 65 by weight (wt %) or less of the fragrance material. For example, the aqueous perfume micro-emulsion composition may include 1 wt % to about 65 wt %, preferably from about 2 wt % to about 50 wt %, and most preferably about 3 wt % to about 40 wt % of such fragrance materials, with respect to the total weight of the aqueous perfume micro-emulsion composition.

The aqueous perfume micro-emulsion composition further comprises water (quantum satis (q.s.)) and may further include one or more optional ingredients. In accordance with an embodiment of the present invention, the water may be process water or purified water (e.g., osmosis, deionized, or distilled). The amount of water in the composition is generally from about 5 wt % to about 95 wt %, preferably from about 10 wt % to about 90 wt % and more preferably from about 20 wt % to about 85 wt %, with respect to the total weight of the aqueous perfume micro-emulsion composition.

Additional optional ingredients, such as antifoaming agents, antioxidants, chelating agents, UV filters, buffers, preservatives, thickening agents, cosmetic active ingredients, moisturizers, humectants, emollients, opacifiers, pearly gloss impacting substances, pigments, colorants, dyes, and/or antifoaming agents, may also be present in the aqueous perfume micro-emulsion composition of the present invention. For example, in an embodiment, an antifoaming agent, such as a dimethylpolysiloxane, may be present to minimize foaming during the micro-emulsion formation process. In another embodiment, a carbonate and/or bicarbonate salt may be combined with water to provide an aqueous carbonate buffer. In yet another embodiment, the carbonate or bicarbonate salt may be present in a sufficient quantity to provide an aqueous buffer having a pH in a range from 4.5 to 8. The optional additional ingredients are generally present in the composition of the present invention from about 0 wt % to about 5 wt %, preferably from about 0.1 wt % to about 3 wt %, and more preferably from about 0.2 wt % to about 1 wt %, with respect to the total weight of the aqueous perfume micro-emulsion composition.

Advantageously, the monoalkyl glycerol ether solvo-surfactants of general formula (I) also possess antimicrobial activity. Thus, in accordance with another embodiment, the transparent, aqueous perfume micro-emulsion composition may be free of additional preservatives, such as free of phenoxylethanol, for example. In yet another embodiment, the transparent, aqueous perfume micro-emulsion composition is free of any antioxidants.

The transparent, aqueous perfume micro-emulsion composition according to the present invention may be prepared by simple mixing, for example, by hand stirring or by using a mechanical mixer, the desired components, and any optional components, to form a homogeneous mixture. The components of the present invention may be added together into a suitable reaction vessel and mixed in any order, using conventional processes well known to those skilled in the art. The micro-emulsion may be produced at room temperature or at an elevated temperature, for example temperatures of 90° C. or less, preferably 55° C. or less, more preferably near room temperature (e.g., 21-25° C.), can be employed.

The aqueous perfume micro-emulsion compositions of the present invention, containing the monoalkyl glycerol ether solvo-surfactant(s), are uniquely useful. The monoalkyl glycerol ether solvo-surfactants have low odor and can be formulated as stable transparent aqueous perfume compositions with high fragrance loading, in several different product forms. Because the monoalkyl glycerol ether(s) have very low odor, they do not change the olfactory profile of the perfume. This allows perfumers to retain the desired odor profile of fully formulated perfumes. The aqueous perfume micro-emulsion compositions containing monoalkyl glycerol ether solvo-surfactant(s) use relatively low quantities of surfactants and as such are pleasant to use with a smooth emollient-like feel without the greasy or tackiness of most presently known perfume micro-emulsions.

The aqueous perfume micro-emulsion compositions can be formulated to be optically clear, and stable from about 5° C. to about 50° C.; and to contain a wide variety of fragrance loadings, for example, from about 1 wt % to about 65 wt % fragrance, preferably from about 2 wt % to about 50 wt %, and most preferably about 3 wt % to about 40 wt % of such fragrance materials. Advantageously, higher fragrance content micro-emulsions may be prepared and subsequently diluted with water to the desired concentration associated with its end-use application, such as fragrances, eaux de toilettes, aqueous perfumes, body sprays, body deodorants, bath products, as well as products such as refreshing and cleaning wet towels, aqueous cosmetic compositions, household cleaners, fabric fragrancers (e.g., scent boosters, softening agents, etc.), air fresheners, and sprayable formulations. Many of these applications require different fragrance loading, and are all easily obtained using the present invention. A single properly formulated perfume micro-emulsion containing the monoalkyl glycerol ether(s) may be diluted with water, for example from about 5 wt % water to about 90 wt % water with no loss of stability, i.e., the resulting product is maintained as a micro-emulsion. Furthermore, aqueous perfume micro-emulsion compositions containing the monoalkyl glycerol ether(s) of general formula (I) can be made stable in spite of the addition of other ingredients such as dyes, gelling agents, iridescent material or sparkling materials.

The following examples are given to illustrate the present invention. Because these examples are presented for illustrative purposes only, the present invention embodied herein should not be limited thereto. Unless otherwise indicated all parts and percentages are by weight.

Examples

Synthesis of Monoalkyl Glycerol Ethers: The solvo-surfactants were synthesized in accordance with a general procedure, where solketal ((2,2-dimethyl-1,3-dioxolan-4-yl) methanol, CAS number 100-79-8) was alkylated with a 1-bromo alkane or 1-bromo alkene, followed by acidic removal of the acetonide protecting group. More specifically, 1 equivalent of solketal and 1.1 equivalents of 1-bromoalkane (or 1-bromoalkene) were dissolved in toluene (to provide ca. 4M solketal), mixed with 1.5 equivalents of potassium hydroxide and 0.05 equivalents of tetrabutyl ammonium bromide, and heated to 80° C. for about 2 hours. Once analysis showed substantial conversion of the solketal, the reaction mixture was removed from heating, diluted with water, and the organic phase was separated and washed with water. The organic phase was concentrated and used in the next step without any further purification. Removal of the acetonide-protecting group may be achieved by treating the crude reaction product with concentrated HCl (ca. 32%) and water, and heating to 40° C. Following cooling the reaction mixture to room temperature, the crude monoalkyl glycerol ether can be isolated from the reaction mixture by extraction with methyl tert-butyl ether (MTBE). The MTBE phase may be washed with saturated $NaHCO_3$ followed by a saturated NaCl solution, and then concentrated under reduced pressure to afford the crude reaction mixture containing the monoalkyl glycerol ethers. Purified monoalkyl glycerol ethers can be isolated from the crude reaction mixture using standard techniques (e.g., crystallization or distillation).

TABLE 1

Synthesized solvo-surfactants 1A-1G.

| | Common name | IUPAC Name | CAS No. |
|---|---|---|---|
| 1A | 1-octyl glycerol ether | 3-octoxypropane-1,2-diol | 10438-94-5 |
| 1B | 1-nonyl glycerol ether | 3-nonoxypropane-1,2-diol | 113676-50-9 |
| 1C | 1-decyl glycerol ether | 3-decoxypropane-1,2-diol | 10430-97-4 |
| 1D | 1-undecyl glycerol ether | 3-undecoxypropane-1,2-diol | 10430-98-5 |
| 1E | 1-dodecyl glycerol ether | 3-dodecoxypropane-1,2-diol | 1561-07-5 |
| 1F | 1-hex-5-enyl glycerol ether | 3-(hex-5-enyloxy)-propane-1,2-diol | 1354252-62-0 |
| 1G | 1-hept-6-enyl glycerol ether | 3-(hept-6-enyloxy)-propane-1,2-diol | n/a |

Transparent aqueous perfume micro-emulsion compositions were formed by mixing the desired quantities of perfume 1 (Table 2 below), solvo-surfactant, surfactant(s), and additives in distilled water at room temperature. Turbidity/transparency of the micro-emulsion compositions were measured at room temperature, on a sample taken at various time intervals and aging temperatures: a) 1.5 h at room temperature, b) 24 h at 5° C. and 50° C., c) 1 week at 5° C. and 50° C., and d) 2 weeks at 5° C. and 50° C. Measurements of turbidity were performed at room temperature on a calibrated (per manufacturer's instructions and standards) turbidimeter: AQUALYTIC® TurbiDirect, taking an average of three (3) measurements done successively with the same sample at room temperature.

TABLE 2

Perfume 1 Composition.

| Chemical Name | Wt % |
|---|---|
| DIPROPYLENE GLYCOL | 45.80 |
| 2,6-DIMETHYLOCT-7-EN-2-OL | 18.67 |
| BICYCLO[2.2.1]HEPTAN-2-OL, 1,7,7-TRIMETHYL-, 2-ACETATE, (1R,2R,4R)-REL- | 6.67 |
| CYCLOPENTANEACETIC ACID, 3-OXO-2-PENTYL, METHYLESTER | 6.67 |
| GERANIOL | 2.67 |
| 9-ACETYL-CEDR-8-ENE | 2.67 |
| CITRONELLOL | 2.67 |
| 3-BUTEN-2-ONE, 3-METHYL-4-(2,6,6-TRIMETHYL-2-CYCLOHEXEN-1-YL)- | 2.67 |
| OCTAHYDRO TETRAMETHYL ACETONAPHTONE | 2.67 |
| 2-PROPENYL 2(3)-METHYLBUTOXYACETATE | 2.00 |
| 1,8-CINEOLE | 1.33 |
| PATCHOULY ESSENTIAL OIL | 1.33 |
| DIMETHYL CYCLOHEXENE CARBOXALDEHYDE | 0.67 |
| 2-(1-METHYLPROPYL)CYCLOHEXANONE | 0.67 |
| DIMETHYL CYCLOHEXENYL PENTENONE | 0.67 |
| CIS-HEX-3-EN-1-OL | 0.40 |
| 7-METHYL-3,4-DIHYDRO-2H-1,5-BENZO-DIOXEPIN-3-ONE | 0.40 |
| 2,6-DIMETHYL-5-HEPTENAL | 0.27 |
| 2-METHYLUNDECANAL | 0.27 |
| 2-DODECAHYDRO-3A,6,6,9A-TETRAMETHYLNAPHTHO[2,1-B]FURAN | 0.27 |
| (1R,3S,7R,8R,10R,13R)-5,5,7,9,9,13-HEXAMETHYL-4,6-DIOXATETRAYCLO(6.5.1.0(1,10).0(3,7))TETRADECANE | 0.27 |
| 2-PROPENYL HEXANOATE | 0.13 |
| 1-PHENYLETHYL ACETATE | 0.13 |
| 1-(2,6,6-TRIMETHYL-3-CYCLOHEXEN-1-YL)-2-BUTEN-1-ONE | 0.07 |
| | 100.0 |

TABLE 3

| Inventive examples (Ex 1-Ex 8). | | | | | | | | |
|---|---|---|---|---|---|---|---|---|
| Example | Ex 1 | Ex 2 | Ex 3 | Ex 4 | Ex 5 | Ex 6 | Ex 7 | Ex 8 |
| Perfume 1 | 55.9 | 15.0 | 55.9 | 15.0 | 47.7 | 15.0 | 50.0 | 50.0 |
| DOSS[a] | 18.6 | 5.0 | 18.6 | 5.0 | 4.4 | 5.0 | 20.0 | 20.0 |
| RH 40[b] | 18.6 | 5.0 | 18.6 | 5.0 | 16.8 | 5.0 | 0.0 | 0.0 |
| 1A | 1.9 | 0.5 | | | | | 0.5 | 0.1 |
| 1B | | | 1.9 | 0.5 | | | | |
| 1C | | | | | 0.2 | 0.2 | | |
| Water | 5.0 | 74.5 | 5.0 | 74.5 | 30.9 | 74.8 | 29.5 | 29.9 |
| wt % | 100.0 | 100.0 | 100.0 | 100.0 | 100.0 | 100.0 | 100.0 | 100.0 |
| Turbidity[c] (NTU) | 1.6 | 4.1 | 2.4 | 4.1 | 8.6 | 5 | 1.1 | 1.2 |
| Turbidity[d] (NTU) | 4.6 | 4.9 | 5.4 | 4.4 | 8 | 5.5 | 0.1 | 0.3 |
| AS:NS [e] | 1.00 | 1.00 | 1.00 | 1.00 | 0.26 | 1.00 | n.a. | n.a. |
| S:P [f] | 0.67 | 0.67 | 0.67 | 0.67 | 0.44 | 0.67 | 0.40 | 0.40 |
| M:S [g] | 0.05 | 0.05 | 0.05 | 0.05 | 0.01 | 0.02 | 0.03 | 0.01 |
| P:(M + S) [h] | 1.43 | 1.43 | 1.43 | 1.43 | 2.23 | 1.47 | 2.43 | 2.49 |

[a]Dioctyl sodium sulfosuccinate, 70% in propylene glycol;
[b]CREMOPHOR ®;
[c]2 weeks at 5° C.;
[d]2 weeks at 50° C.;
[e] AS:NS = mass ratio of anionic surfactant to nonionic surfactant;
[f] S:P = mass ratio of surfactant(s) to perfume;
[g] M:S = mass ratio of monoalkyl glycerol ether to surfactant; and
[h] P:(M + S) = mass ratio of perfume to sum of monoalkyl glycerol ether and surfactant(s).

TABLE 3

| Inventive examples (Ex 9-Ex 15). | | | | | | | |
|---|---|---|---|---|---|---|---|
| Example | Ex 9 | Ex 10 | Ex 11 | Ex 12 | Ex 13 | Ex 14 | Ex 15 |
| Perfume 1 | 23.9 | 9.6 | 15.0 | 48.7 | 48.7 | 50.0 | 14.9 |
| DOSS[a] | 9.4 | 4.6 | 8.0 | 20.0 | 20.0 | 20.0 | 4.9 |
| RH 40[b] | 3.0 | 18.2 | 3.0 | 18.6 | 18.6 | 5.6 | 20.0 |
| 1D | 2.0 | 2.3 | | | | | |
| 1E | | | 1.0 | | | | |
| 1F | | | | 0.2 | 0.1 | | |
| 1G | | | | | | 0.1 | 2.3 |
| Water | 61.7 | 65.3 | 73.0 | 12.5 | 12.6 | 24.3 | 57.9 |
| wt % | 100.0 | 100.0 | 100.0 | 100.0 | 100.0 | 100.0 | 100.0 |
| Turbidity[c] (NTU) | 6.3 | 3 | <12 | 0.1 | 0.1 | 0.4 | 1.1 |
| Turbidity[d] (NTU) | 5.2 | 3.2 | <12 | 0.1 | 0.1 | 0.4 | 0.8 |
| AS:NS [e] | 3.13 | 0.25 | 2.67 | 1.08 | 1.08 | 3.57 | 0.25 |
| S:P [f] | 0.52 | 2.38 | 0.73 | 0.79 | 0.79 | 0.51 | 1.67 |
| M:S [g] | 0.16 | 0.10 | 0.09 | 0.01 | 0.003 | 0.004 | 0.09 |
| P:(M + S) [h] | 1.66 | 0.38 | 1.25 | 1.26 | 1.26 | 1.95 | 0.55 |

[a]Dioctyl sodium sulfosuccinate, 70% in propylene glycol;
[b]CREMOPHOR ®;
[c]2 weeks at 5° C.;
[d]2 weeks at 50° C.;
[e] AS:NS = mass ratio of anionic surfactant to nonionic surfactant;
[f] S:P = mass ratio of surfactant(s) to perfume;
[g] M:S = mass ratio of monoalkyl glycerol ether to surfactant; and
[h] P:(M + S) = mass ratio of perfume to sum of monoalkyl glycerol ether and surfactant(s).

To prepare inventive examples 1, 3, and 5-19, components (perfume, solvo-surfactant 1A-1G, surfactant(s)) listed in Table 2, 3, or 4 are mixed with distilled water until transparent micro-emulsions form. The inventive examples remained stable at two weeks at 5° C. and 50° C. Examples 2 and 4 were prepared by taking an aliquot (26.8%) of Examples 1 and 3, respectively, diluted with distilled water (73.2%) to provide transparent micro-emulsions, which also remained stable at two weeks at 5° C. and 50° C.

TABLE 4

Comparative examples (C-1 to C-4) and inventive examples (Ex16-19).

| Example | C-1 | C-2 | C-3 | C-4 | Ex 16 | Ex 17 | Ex 18 | Ex 19 |
|---|---|---|---|---|---|---|---|---|
| Perfume 1 | 15.00 | 15.00 | 15.00 | 15.00 | 15.00 | 55.90 | 15.00 | 55.90 |
| DOSS [a] | 5.00 | 5.00 | 5.00 | 5.00 | 5.00 | 18.60 | 5.00 | 18.60 |
| RH 40 [b] | 5.00 | 5.00 | 5.00 | 5.00 | 5.00 | 18.60 | 5.00 | 18.60 |
| 1,2-HD [c] | 0.5 | | | | | | | |
| Butyl MAGE [d] | | 0.5 | | | | | | |
| Pentyl MAGE [e] | | | 0.5 | | | | | |
| Hexyl MAGE [f] | | | | 0.5 | | | | |
| 1A | | | | | 0.50 | 1.90 | | |
| 1C | | | | | | | 0.50 | 1.90 |
| Water | 74.50 | 74.50 | 74.50 | 74.50 | 74.50 | 5.00 | 74.50 | 5.00 |
| wt % | 100.00 | 100.00 | 100.00 | 100.00 | 100.00 | 100.00 | 100.00 | 100.00 |
| Turbidity [g] (NTU) | 4.0 | 4.0 | 3.9 | 4.1 | 3.8 | 1.6 | 3.7 | 2.4 |
| Turbidity [h] (NTU) | 4.7 | 4.3 | 4.4 | 4.2 | 3.8 | 4.6 | 3.9 | 5.4 |

[a] Dioctyl sodium sulfosuccinate, 70% in propylene glycol;
[b] CREMOPHOR ®;
[c] 1,2-hexanediol;
[d] 3-butoxypropane-1,2-diol;
[e] 3-pentoxypropane-1,2-diol;
[f] 3-hexoxypropane-1,2-diol;
[g] 2 weeks at 5° C.;
[h] 2 weeks at 50° C.

In order to assess efficiency, comparative examples C-1 through C-4 were prepared by replacing the inventive solvo-surfactants with 1,2-hexanediol, 1-butyl glycerol ether, 1-pentyl glycerol ether, and 1-hexyl glycerol ether, respectively. The components listed in Table 4 were mixed with distilled water until transparent micro-emulsions form. Turbidity measurements of samples aged for two weeks at 5° C. and 50° C. confirmed that the inventive solvo-surfactants produce stable, transparent, aqueous perfume micro-emulsion compositions with similar efficiencies to that of prior art compounds, despite being significantly less water-soluble.

Unless otherwise explained, all technical and scientific terms used herein have the same meaning as commonly understood by one of ordinary skill in the art to which this disclosure belongs. In case of conflict, the present specification, including explanations of terms, will control. The singular terms "a," "an," and "the" include plural referents unless context clearly indicates otherwise. Similarly, the word "or" is intended to include "and" unless the context clearly indicates otherwise. The term "comprising" means "including;" hence, "comprising A or B" means including A or B, as well as A and B together.

While the invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative product and/or method and examples shown and described. The various features of exemplary embodiments described herein may be used in any combination. Accordingly, departures may be made from such details without departing from the scope of the general inventive concept.

The invention claimed is:

1. A transparent, aqueous perfume micro-emulsion composition comprising:

(a) a fragrance material, wherein the fragrance material is present in an amount within a range of 3 wt % to 65 wt %;

(b) a solvo-surfactant, wherein the solvo-surfactant comprises a monoalkyl glycerol ether having a general formula (I) of R—O—CH2-CH(OH)—CH2OH, wherein R is a C6 to C7 unbranched terminal alkenyls, wherein the solvo-surfactant is present in an amount within a range of 0.1 wt % to 25 wt %;

(c) an ionic surfactant present in an amount within the range of 0.5 wt % to 20 wt %;

(d) a non-ionic surfactant present in an amount within the range of 0 wt % to 20 wt %; and (e) quantum satis (q.s.) water;

wherein wt % is based on the total weight of the micro-emulsion composition, and wherein the composition is substantially free of ethanol.

2. The aqueous perfume micro-emulsion composition according to claim 1, wherein a mass ratio between a mass of the fragrance material and a combined mass of the solvo-surfactant, the ionic surfactant, and the non-ionic surfactant is greater than 1.

3. The aqueous perfume micro-emulsion composition according to claim 1, wherein the ionic surfactant is selected from the group consisting of anionic surfactants, cationic surfactants, zwitterionic surfactants, and combinations thereof.

4. The aqueous perfume micro-emulsion composition according to claim 1, wherein the ionic surfactant comprises an anionic surfactant.

5. The aqueous perfume micro-emulsion composition according to claim 1, wherein the ionic surfactant comprises a dialkyl sulfosuccinate, preferably dioctyl sulfosuccinate.

6. The aqueous perfume micro-emulsion composition according to claim 1, wherein the ionic surfactant comprises a cationic surfactant.

7. The aqueous perfume micro-emulsion composition according to claim 1, wherein the ionic surfactant comprises a quaternary ammonium surfactant, preferably cetrimonium chloride.

8. The aqueous perfume micro-emulsion composition according to claim 1, wherein the non-ionic surfactant is selected from the group consisting of polyethoxylated hydrogenated castor oils.

9. The aqueous perfume micro-emulsion composition according to claim 1, wherein the non-ionic surfactant comprises PEG-40 hydrogenated castor oil.

10. The aqueous perfume micro-emulsion composition according to claim 1, wherein the ionic surfactant comprises dioctyl sulfosuccinate; and wherein the non-ionic surfactant comprises PEG-40 hydrogenated castor oil.

11. The aqueous perfume micro-emulsion composition according to claim 1, further comprising a carbonate-based buffer to provide pH in a range from 4.5 to 8.

12. The aqueous perfume micro-emulsion composition according to claim 1, further comprising:

an antifoaming agent in a sufficient quantity to minimize foaming; and/or 1,2-hexanediol.

13. A method of preparing the transparent, aqueous perfume micro-emulsion composition according to claim 1 comprising mixing the fragrance material, solvo-surfactant, ionic surfactant and non-ionic surfactant in the water.

* * * * *